United States Patent

Bessa Bellmunt et al.

(10) Patent No.: US 7,179,913 B2
(45) Date of Patent: Feb. 20, 2007

(54) PROCESS FOR PREPARING A PHARMACEUTICALLY ACTIVE COMPOUND AND FOR PREPARING ITS INTERMEDIATE

(75) Inventors: Jordi Bessa Bellmunt, Barcelona (ES); Pere Dalmases Barjoan, Sant Feliu De Llobregat (ES)

(73) Assignee: Vita Cientifica, S.A., Sant Joan Despi (Barcelona) (ES)

( * ) Notice: Subject to any disclaimer, the term of this patent is extended or adjusted under 35 U.S.C. 154(b) by 0 days.

(21) Appl. No.: 10/532,397

(22) PCT Filed: Oct. 27, 2003

(86) PCT No.: PCT/IB03/04763

§ 371 (c)(1),
(2), (4) Date: Apr. 22, 2005

(87) PCT Pub. No.: WO2004/039767

PCT Pub. Date: May 13, 2004

(65) Prior Publication Data

US 2006/0052625 A1  Mar. 9, 2006

(30) Foreign Application Priority Data

Oct. 31, 2002  (ES)  ................................ 200202502

(51) Int. Cl.
C07D 253/075  (2006.01)
C07C 255/03  (2006.01)
(52) U.S. Cl. ...................................... 544/206; 558/391
(58) Field of Classification Search ................. 544/206; 558/391
See application file for complete search history.

(56) References Cited

FOREIGN PATENT DOCUMENTS

| EP | 0021121 | 5/1983 |
|---|---|---|
| EP | 0247892 | 4/1991 |
| EP | 1127873 | 8/2001 |
| EP | 0963980 | 6/2002 |
| WO | 0035888 | 6/2000 |
| WO | 0149669 | 7/2001 |
| WO | 03078407 | 9/2003 |
| WO | 2004/026845 A1 * | 4/2004 |

* cited by examiner

*Primary Examiner*—Taofiq Solola
(74) *Attorney, Agent, or Firm*—Wolf Block Schorr & Solis-Cohen LLP

(57) ABSTRACT

The invention discloses a method for preparing the intermediate 2-(2,3-dichlorophenyl)-2-(aminoguanidine)acetonitrile of formula (II), which comprises the reaction of 2,3-dichlorobenzoyl cyanide with aminoguanidine bicarbonate in non-aqueous medium in the presence of methanesulphonic acid, which produces good yields and short reaction times.

Said intermediate is useful for preparing 3,5-diamino-6-(2, 3-dichlorophenyl)-1,2,4-triazine of formula (I). The invention also relates to a method for preparing (I) with high purity

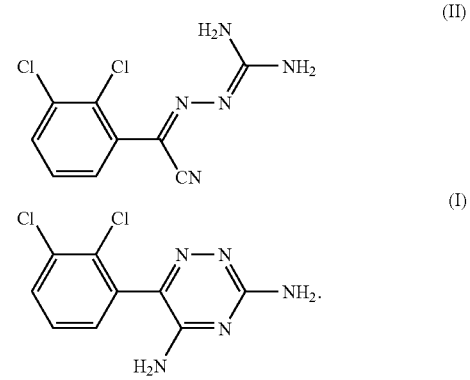

6 Claims, No Drawings

PROCESS FOR PREPARING A PHARMACEUTICALLY ACTIVE COMPOUND AND FOR PREPARING ITS INTERMEDIATE

FIELD OF THE INVENTION

This invention relates to a new method for preparing an intermediate useful in turn for preparing a pharmaceutically active compound with antiepileptic properties, and a method for making said pharmaceutically active compound.

BACKGROUND OF THE INVENTION

Patent EP 21121 describes 3,5-diamino-6-(substituted phenyl)-1,2,4-triazines which are active in central nervous system disorders such as psychiatric and neurological disorders, and are particularly useful as anticonvulsants, for example in the treatment of epilepsy. Of these, the preferred compound is 3,5-diamino-6-(2,3-dichlorophenyl)-1,2,4-triazine, of formula (I):

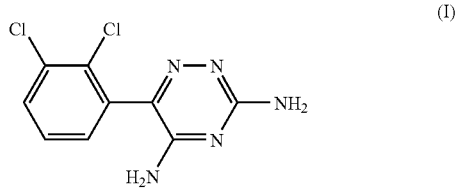

This compound is commonly known as lamotrigine and is marketed as an anti-epileptic drug.

The said European patent discloses the preparation of lamotrigine by the reaction of 2,3-dichlorobenzoyl cyanide with aminoguanidine bicarbonate to give the intermediate 2-(2,3-dichlorophenyl)-2-(aminoguanidine)acetonitrile, of formula (II):

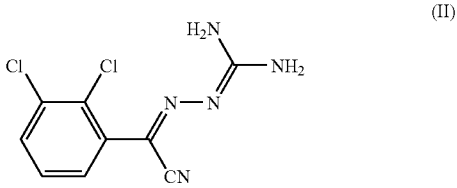

which by cyclisation, in an aliphatic alcohol under reflux in the presence of a strong base, yields lamotrigine.

The preparation of the intermediate of formula (II) by reaction of 2,3-dichlorobenzoyl cyanide with aminoguanidine bicarbonate is carried out in said patent EP 21121 in an aqueous solution of nitric acid in the presence of dimethyl sulphoxide. Subsequently, patents EP 247892, EP 963980 and WO 0035888 described the same reaction for preparing the intermediate of formula (II), but in this case in an aqueous solution of sulphuric acid and with acetonitrile as solvent.

The method described for preparing said intermediate nevertheless has disadvantages of an environmental type, since it uses solvents such as dimethyl sulphoxide and acetonitrile, and of an economic type due to it being an excessively slow reaction. In the aqueous medium in which the reaction is carried out and under the conditions described in that method, the 2,3-dichlorobenzoyl cyanide has a tendency to hydrolyse and its reaction with aminoguanidine bicarbonate is too slow, requiring 2 to 7 days, after which time the yield obtained is only 15% to 60%.

European patent application EP 1127873 has the object of improving said method for preparing the intermediate by carrying out the reaction in a non-aqueous medium using polyphosphoric acid and with acetonitrile as solvent. However, this method still presents the same environmental disadvantages, since it also uses toxic solvents, as well as economic disadvantages in that, although the reaction time has been reduced to approximately 20 h, the reaction remains slow.

International patent application WO 0149669 describes the same reaction for preparing the intermediate of formula (II) using 2,3-dichlorobenzoyl cyanide and aminoguanidine bicarbonate, but in this case in the presence of concentrated sulphuric acid and p-toluenesulphonic acid in toluene at 80° C. Although under such conditions a reduced reaction time is achieved, it is nevertheless necessary to employ high temperatures, with the disadvantages this entails, such as the formation of decomposition or degradation by-products. Moreover, this method still has disadvantages of an economic type, since the yields obtained are of the order of 50%.

Furthermore, in the methods described above for preparing the intermediate, once the reaction has finished the acid suspension is filtered directly, without taking into account the traces of hydrogen cyanide produced as a reaction by-product.

The preparation of lamotrigine by cyclisation of the intermediate of formula (II), as noted above, was initially disclosed in patent EP 21121, refluxing in an alcohol in the presence of a strong base. This cyclisation reaction was subsequently disclosed in aliphatic alcohol under reflux in the absence of a base in the following European patents: EP 247892, EP 963980, EP 1127873. However, in order to prepare an end product of high purity, patents EP 963980, WO 0035888 and WO 0149669 disclosed that following such cyclisation one or more steps of recrystallisation are required, with the disadvantages this involves, such as yield losses, following which disclosed purities of only 99.1%, or at best 99.7%, are achieved.

Due to all this, and taking account of the prior art described, it is still necessary provide a method for preparing the intermediate of formula (II) and, therefore, of preparing lamotrigine, which is fast, cheap, safe and offers good yields.

DESCRIPTION OF THE INVENTION

A first aspect of this invention is to provide a new method for preparing the intermediate 2-(2,3-dichlorophenyl)-2-(aminoguanidine)acetonitrile, of formula (II):

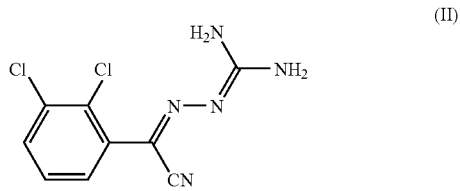

which comprises the reaction of 2,3-dichlorobenzoyl cyanide with aminoguanidine bicarbonate, characterised in that it is carried out in a non-aqueous medium in the presence of methanesulfonic acid.

Surprisingly, the authors of this invention have found that the use of methanesulphonic acid in preparing the intermediate of formula (II) means that the presence of other solvents as reaction medium is not required, for the acid itself acts as reaction medium, giving rise to good yields and shorter reaction times.

The method of the invention thus overcomes the problems related with the use of solvents not recommended for use on an industrial scale due to their harmful effects for the environment. The method also allows the reaction volume to be reduced.

Alternatively, it is also possible to dissolve the initial reagent, 2,3-dichlorobenzoyl cyanide, in a solvent that permits the preparation of concentrated solutions of 2,3-dichlorobenzoyl cyanide and in which the intermediate of formula (II) is not soluble, such as toluene.

Although the method of the invention can be carried out within a temperature range of 20–80° C., it is preferable for the reaction to take place at a temperature between 30° and 60° C. This means it is a reaction that occurs at low temperatures and is, therefore, a cheaper method.

Advantageously, the method of the invention permits preparation of the intermediate of formula (II) with high yields, of the order of 80%, at low temperatures, and in only some 5 h.

Preferably, the method of the invention comprises, once the reaction has finished and before filtering and isolation of the intermediate 2-(2,3-dichlorophenyl)-2-(aminoguanidine)acetonitrile, of formula (II), by conventional methods, an additional step that comprises the addition of water and subsequent adjustment of the pH of the medium until a pH higher than the pKa of the hydrogen cyanide (9.31)is achieved.

Preferably, the pH is adjusted by adding an aqueous solution of a strong base such as sodium hydroxide.

Advantageously, the fact that the pH of the medium is adjusted to a pH higher than the pKa of the hydrogen cyanide allows the traces of hydrogen cyanide produced in the reaction to be neutralised, which ensures filtering and isolation of the reaction product under safe conditions.

This invention also relates to a method for preparing lamotrigine which comprises preparation of the intermediate of formula II as defined in the first aspect of the invention.

A second aspect of this invention is therefore to provide a method for preparing the 3,5-diamino-6-(2,3-dichlorophenyl)-1,2,4-triazine, of formula (I):

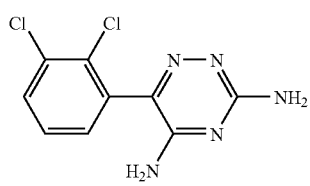

or a pharmaceutically acceptable salt thereof, which comprises the following steps:

a) reaction of 2,3-dichlorobenzoyl cyanide with aminoguanidine bicarbonate in non-aqueous medium in the presence of methanesulphonic acid, to give the intermediate 2-(2,3-dichlorophenyl)-2-(aminoguanidine)acetonitrile, of formula (II):

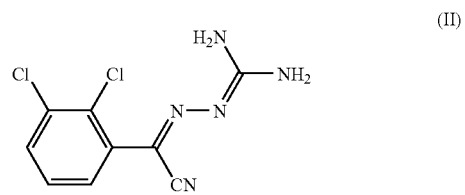

b) cyclisation of the intermediate 2-(2,3-dichlorophenyl)-2-(aminoguanidine)acetonitrile of formula (II) in an aliphatic alcohol or in an aliphatic alcohol/water solution under reflux and, if desired, obtaining a pharmaceutically acceptable salt thereof.

Preferably, said step b) is carried out by refluxing in an aliphatic alcohol. More preferably still, said aliphatic alcohol is chosen from between ethanol and isopropanol.

Advantageously, the preparation of 3,5-diamino-6-(2,3-dichlorophenyl)-1,2,4-triazine of formula (I) from the intermediate of formula (II) prepared according to the first aspect of the invention, permits a method to be carried out for preparing the compound of formula (I) with high yields and with a very high purity, even exceeding 99.9%, without any need for recrystallisation. All it needs is a washing to eliminate possible colouration from the end product.

Experimental Part

Provided below, by way of non-restrictive explanation of the invention, are the following examples.

EXAMPLES OF SYNTHESIS

Example 1

2-(2,3-dichlorophenyl)-2-(aminoguanidine)-acetonitrile 400 g (2 moles) of 2,3-dichlorobenzoyl cyanide are added to a mixture prepared from 333.6 g (2.45 moles) of aminoguanidine bicarbonate in 800 mL of methanesulphonic acid. The mixture is then heated at 45° C. for 5 hours, cooled to 10° C. and 2.4 L of water is added slowly, controlling exothermy at 20–30° C. The mixture is then adjusted to pH 11 with a 50% NaOH solution, filtered, the solid washed with water and dried at 45° C. to yield 419.8 g (82%) of the product of the title.

NMR $^1$H (DMSO), δ (ppm): 6.5–6.9 (s, 4H, —N=C(NH$_2$)$_2$), 7.4 (t, 1H, ArH), 7.6 (d, 2H, ArH). M.p.=180–183° C.

Example 2

2-(2,3-dichlorophenyl)-2-(aminoguanidine)-acetonitrile

To a mixture prepared from 4.2 g (0.031 moles) of aminoguanidine bicarbonate in 10 mL of methanesulphonic acid is added a solution of 5 g (0.025 moles) 2,3-dichlorobenzoyl cyanide in 5 mL of toluene. The mixture is heated at 45° C. for 10 hours, cooled to 10° C. and 30 mL of water added slowly, controlling exothermy at 20–30° C. The mixture is then adjusted to pH 11 with a 40% NaOH solution, filtered, the solid washed with water and dried at 45° C. to yield 5.05 g (79%) of the product of the title.

Example 3

3,5-diamino-6-(2,3-dichlorophenyl)-1,2,4-triazine

A mixture made up of 100 g of 2-(2,3-dichlorophenyl)-2-(aminoguanidine)-acetonitrile cyanide as prepared in Example 1 and 1000 mL of absolute ethanol is heated under reflux for 6 h. After cooling to 0–5° C. the mixture is filtered, the solid obtained washed with 500 mL of absolute ethanol under reflux and dried at 80° C. in a vacuum oven to yield 83 g (83%) of the product of the title.

NMR $^1$H (DMSO), δ (ppm): 6.4 (s, 2H, —NH$_2$), 6.5–7.0 (s, 2H, —NH$_2$), 7.3–7.5 (m, 2H, ArH), 7.7 (d, 1H, ArH). M.p.=217° C.

Purity (HPLC): exceeds 99.9%.

Example 4

3,5-diamino-6-(2,3-dichlorophenyl)-1,2,4-triazine

Following the method described in Example 3, but using 1200 mL of isopropyl alcohol instead of the 1000 mL of ethanol, 90 g (90%) of the product of the title is obtained.

Example 5

3,5-diamino-6-(2,3-dichlorophenyl)-1,2,4-triazine

Following the method described in Example 3, but using 500 mL of isopropyl alcohol and 188 mL of water instead of the 1000 mL of ethanol, 82 g (82%) of the product of the title is obtained.

Example 6

3,5-diamino-6-(2,3-dichlorophenyl)-1,2,4-triazine

Following the method described in Example 3, but using ethanol 96% instead of ethanol, 90 g (90%) of the product of the title is obtained.

What is claimed is:

1. A process for preparing the intermediate 2-(2,3-dichlorophenyl)-2-(aminoguanidine)acetonitrile, of formula (II):

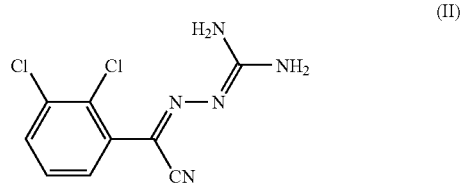

which comprises the reaction of 2,3-dichlorobenzoyl cyanide with aminoguanidine bicarbonate, wherein it is carried out in non-aqueous medium in the presence of methanesulphonic acid as the only reaction medium; and wherein once the reaction has finished, the process further comprises the steps of:
   i) adding water;
   ii) adjusting the pH of the medium to a pH higher than the pKa of hydrogen cyanide; and
   iii) isolating intermediate of formula (II).

2. Process according to claim 1, wherein said reaction is carried out within a temperature range of 20 to 80° C.

3. Process according to claim 2, wherein said reaction is carried out within a temperature range of 30 to 60° C.

4. Process according to claim 1, wherein in ii), said adjustment of the pH is carried out by adding a sodium hydroxide solution.

5. Process for preparing the 3,5-diamino-6-(2,3-dichlorophenyl)-1,2,4-triazine, of formula (I):

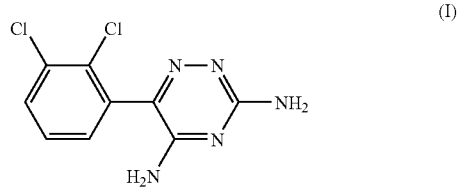

or a pharmaceutically acceptable salt thereof, which comprises the following steps:
   a) preparation of the intermediate 2-(2,3-dichlorophenyl)-2-(aminoguanidine)acetonitrile, of formula (II), according to claim 1;
   b) cyclisation of said intermediate of formula (II) in an aliphatic alcohol or in an aliphatic alcohol/water solution under reflux; and, if desired, obtaining a pharmaceutically acceptable salt thereof.

6. Process according to claim 5, wherein said aliphatic alcohol used in step b) may be chosen from between ethanol and isopropanol.

* * * * *